United States Patent [19]

Horak et al.

[11] 4,291,133

[45] Sep. 22, 1981

[54] NONTHROMBOGENIC POLYMER SURFACE

[76] Inventors: Vaclav Horak, 5508 Oakmont Ave., Bethesda, Md. 20034; Jiri Janata, 2231 Logan Ave., Salt Lake City, Utah 84108

[21] Appl. No.: 27,366

[22] Filed: Apr. 5, 1979

[51] Int. Cl.$^3$ .................. C08L 35/00; C08L 27/06; C08L 27/12

[52] U.S. Cl. ........................................ 525/74; 525/66; 525/70; 525/78; 525/207; 525/221; 525/232; 525/238; 525/239; 525/240; 525/241; 428/515; 424/78; 424/183

[58] Field of Search ............... 525/207, 74, 221, 232, 525/238, 239, 240, 241, 66, 78, 70; 424/183, 78; 428/515

[56] References Cited

U.S. PATENT DOCUMENTS

| | | |
|---|---|---|
| 3,475,358 | 10/1969 | Bixler et al. ........................ 424/183 |
| 3,617,344 | 11/1971 | Leininger et al. .................. 424/183 |
| 3,673,612 | 7/1972 | Merrill et al. ...................... 424/183 |
| 3,755,218 | 8/1973 | Yen et al. ........................... 424/183 |
| 3,826,678 | 7/1974 | Hoffman et al. ................... 424/183 |
| 3,844,989 | 10/1974 | Harumiya et al. ................. 424/183 |
| 3,846,353 | 11/1974 | Grotta ................................ 424/183 |

*Primary Examiner*—Carman J. Seccuro
*Attorney, Agent, or Firm*—Trask & Britt

[57] ABSTRACT

Polymer surfaces which are rendered nonthrombogenic are disclosed. Polymers, including hydrophobic polymers, which can be swollen by selected solvents, are rendered nonthrombogenic by absorbing into the surface of said polymers pendant aliphatic side chains which are attached to a linear polymer having reactive pendant groups which are negatively charged or which may be reacted with compounds having a negative charge, such as heparin. The compounds absorbed into the substrate surface have multi-point attachment to the surface.

10 Claims, No Drawings

NONTHROMBOGENIC POLYMER SURFACE

BACKGROUND OF INVENTION

1. Field

This invention relates to polymers which are surface modified by attachment of compounds having groups absorbable into said surface and reactive groups by absorption of the compatible groups into the surface area of the polymers.

2. Prior Art

Polymer surfaces, particularly hydrophobic polymer surfaces, have been treated in various ways to render the polymer surface nonthrombogenic so that plastic materials may be utilized with less risk in the field of artificial organs and prosthetic devices.

One such surface modification treatment is described by Froehling et al, *Uptake of Tridodecylmethylammonium Chloride by PVC*, Journal of Applied Polymer Science, Vol, 21, 2855-2859 (1977). The molecules to be absorbed appear to repel each other, limiting the number of groups which can be attached to a given surface area of substrate. Quaternary ammonium salt, i.e., tridodecylmethylammonium chloride (TDMAC) has been absorbed into a substrate to provide an ion exchange capacity which can be used to ionically bond heparin. This general approach is also disclosed in U.S. Pat. No. 3,617,344 of Leininger et al. A similar technique is described in U.S. Pat. No. 3,549,409 of Dyck et al wherein a polyvalent metal salt is absorbed upon a plastic surface to provide sites for heparinization.

Another approach has been to synthesize polymers which directly absorb heparin, thus enabling construction of plastic articles which may be directly heparinized. Modified poly-amido-amine block copolymers have been prepared; *A New Nonthrombogenic Polymeric Material* Ferruti and Provenzale, Transplantion Proceedings, Vol. VIII, No. 1, March 1976.

OBJECTS OF THE INVENTION

It is an object of the instant invention to provide an improved polymer surface having stable, nonthrombogenic activity.

Another object of the instant invention is to provide a nonthrombogenic surface by multi-point attachment of a polymer modifier by means of linear aliphatic chains which penetrate the substrate polymer surface.

A further objective of the invention is to provide a polymer substrate with a variety of reactive sites.

Another object of the invention is to provide a polymer substrate with a predetermined density of reactive sites.

SUMMARY OF THE INVENTION

The instant invention involves a surface modified polymeric substrate which is swellable by selected solvents and a branched-chain polymer having a substantially linear backbone, a plurality of substantially linear aliphatic pendant chains and a plurality of pendant reactive groups, said linear aliphatic pendant chains being substantially embedded in the polymeric substrate. Thus, the surface modified polymer substrate, which is frequency composed of a hydrophobic polymer, has a number of "legs" of hydrocarbon chains, which are spaced along the backbone of a linear polymer, embedded in the polymer to a substantially uniform depth. The "legs" cannot be embedded into the polymer any further than the length of the legs since the backbone linear polymer will prevent any further penetration. Opposite to the "legs" and attached to the linear polymer and in a position to float freely to be available for further reaction, are certain other pendant groups which contain reactive sites.

A significant advantage of the instant invention is the modification of polymeric surfaces which are normally nonreactive to form a reactive surface whereby the reactive sites have a predetermined spacing and whereby the surface density of the reactive sites can be substantially controlled. A particular advantage to this invention is that hydrophobic polymeric surfaces can be rendered nonthrombogenic by the absorption thereon of pendant groups of a linear polymer which has pendant reactive groups which are negatively charged or which may be reacted with compounds having a negative charge, such as heparin. A significant feature of the invention is that the mechanical properties of the substrate remain unaffected while the surface properties can be altered. Thus, polymers which are readily used in industry for various purposes and which have known mechanical strength, stability, and formable properties and the like may be readily used to form new implements wherein the surface may be modified to achieve a particular result yet maintain the dependability and assurance of the properties of the substrate.

The instant invention is particularly advantageous inasmuch as bulk polymeric surfaces which are primarily hydrophobic in nature may be modified so that the surface becomes hydrophilic and further that the surface may become reactive to a particular type of compound. Thus, the surface may be modified to tailor-fit a particular situation.

Polymeric substrate surfaces which may be readily used in the instant invention are swellable plastics such as polyethylene, polypropylene, nylon, polyvinylchloride, rubbers and elastomers such as polybutadiene, polystyrene, polyacrylonitrile and copolymers thereof and similar hydrophobic polymers, and the like. In general, these are thermoplastic polymers and further are generally swellable by certain solvents. The solvent action is necessary to expand the surface of the substrate so that it will admit or absorb linear aliphatic chains which are dissolved in or carried by the solvent.

Solvents which may be utilized in the following invention include many of the following, although it is readily known in the art as to solvents which will swell the more commonly used hydrophobic polymers. For example, some solvents which will swell polyethylene and polypropylene surfaces are: chlorobenzene, orthodichlorobenzene and the like.

Solvents which swell polyvinylchloride, and similar substrates are: toluene, hexane, and the like. Polybutadienestyrene copolymers are swellable by: cyclohexane, pentane, toluene and the like.

A further understanding of the invention may be facilitated by reference to FIG. 1 which shows a polymeric substrate with a linear polymer having absorbable groups in proximity thereto. The linear polymer in this instance is one which has a four carbon repeating group which has attached to the first (or second) carbon atom a linear aliphatic hydrocarbon chain of sixteen carbons in length. Attached to the third and fourth carbon atoms of the repeating unit is a reactive group such as an anhydride group. The repeating unit repeats a number of times according to the number n which represents an integer from about 5 to about 100 and preferably from about 10 to about 80.

In FIG. 2 the linear polymer is shown having the pendant aliphatic group absorbed into the surface of the substrate. The degree to which the surface absorption takes place depends upon the swelling power of the solvent, the concentration of the modifying polymers in the solvent, and the time of exposure, and the temperature of the solvent. The degree of absorption of the pendant aliphatic groups can be moderately controlled by regulating the above mentioned variables. The polymer backbone acts as a stop limiting absorbtion to the pendant aliphatic group.

The representation of FIG. 3 shows a structure for the linear polymer with pendant groups. The letter "a" indicates the length of the pendant, aliphatic groups. Generally, it is greatly preferred that each pendant, aliphatic group be of the same length. The length of a pendant, aliphatic group may be varied as desired, for example, the length may be from about six to about 20 with about 6 to 12 being preferred. The longer the pendant, aliphatic group is, the more deeply it may be absorbed and the more securely the linear backbone polymer becomes anchored to the substrate. Pendant groups which are too long, for example, over 20, may fold upon themselves and be difficult to absorb. However, for some purposes a short, pendant, aliphatic group may be preferred since it may be absorbed completely in a relatively short period of time so that the polymer backbone may be in close proximity to the bulk polymer substrate surface.

The letter "b" represents the spacing between the two pendant aliphatic groups, which again will determine to some extent the degree to which the linear polymer backbone is anchored to the substrate. The spacing between adjacent pendant, aliphatic groups should be sufficient so that the aliphatic groups will not have a significant tendency to become intertwined or compete for absorption into the same site in the substrate surface. Generally, a spacing of about four carbon atoms or more is preferred. However, if the spacing is too great, for example, more than about ten to twelve carbon atoms separating adjacent aliphatic group, the plural anchoring effect, which is a significant aspect of the instant invention, could be substantially lost. Generally, it is preferred that the spacing between pendant aliphatic groups be from about three to about eight carbon atoms.

The letter "c" indicates the length of the pendant reactive group. As illustrated in FIGS. 1 and 2, the length of the pendant reactive group, i.e., arm, is only one carbon atom from the polymer backbone. For certain applications, the length may be up to about 12 carbon atoms. The letter "d" represents the spacing between reactive arms attached to the polymer backbone. This spacing acts as a further regulation of density of reactive sites.

Generally, the polymer backbone will be attached via a cooperative, synergystic mechanism, i.e., a "zipper" effect. Once one pendant aliphatic group is absorbed it brings the adjacent pendant aliphatic group in sufficient proximity to the polymer surface that it will become absorbed preferentially and the polymer backbone will thus be "zipped" onto the substrate surface.

As illustrated in FIG. 3, the number of reactive sites may be varied on the polymer backbone so that the density of reactive sites on the substrate surface may be substantially controlled. Also, the length of the pendant chain carrying the reactive group will affect its reactivity, to some extent, with other compounds. For reaction with other compounds, it is generally preferred that the reactive group be spaced a plurality of carbon atoms, for example, at least six carbon atoms, from the polymer backbone so that there is very little problem with steric hindrance or the like whenever a large reactive molecule is intended to be attached to the reactive site of the backbone polymer. Generally, for the purposes of this invention, it is not particularly advantageous to have a reactive site which is attached by a pendant group of more than about twelve atoms spacing from the polymer backbone. However, for introducing negative charges onto the hydrophobic surface, it is preferred that the reactive groups are attached directly to the linear polymer backbone.

One compound which can be readily utilized in the instant invention having reactive sites is polyanhydride PA-18 of Gulf Research, Inc. This compound has a structure substantially identical to the structure illustrated in FIG. 1 wherein it has repeating groups, anhydride groups, attached to the backbone. The average molecular weight of PA-18 is about 22,500, and there are about 68 anhydride groups per average backbone polymer molecule. Polyanhydride polymer PA-18 is soluble in the following preferred solvents: cyclohexane, toluene.

Polyanhydride PA-18 may be readily attached to substrates of polyvinylchloride, polyethylene, polypropylene, rubbers, elastomers, and the like.

Other modifying polymers may have molecular weights of from about 2,000 to about 30,000.

A further instance of use of the instant invention is to place a negative surface charge on the substrate surface to inhibit polymerization of fibrinogen to fibrin and thus prevent the formation of blood clotting. Heparin, a sulphonated polysaccharide, is widely used for this purpose. Polyvinyl chloride treated with polymer PA-18 which is subsequently hydrolyzed to yield high density of carboxylic groups does not induce clotting in nonheparinized blood.

EXAMPLE

A polyvinylchloride catheter was swollen in a mixture of toluene, petrol ether and acetone, containing 5% weight by volume of polymer PA-18 for five minutes. After de-swelling the catheter was washed with acetone to remove residual PA-18 polymer and placed in water for twelve hours to hydrolyze the anhydride. The catheter was then placed in dog blood for six hours with no clotting being observed. An untreated control catheter was similarly placed in dog blood and clotting was observed within 10–20 minutes.

We claim:
1. A surface-modified polymeric substrate comprising:
 a polymeric hydrophobic substrate swellable by selected solvents: and
 a branched-chain polymer having a substantially linear hydrocarbon backbone, substantially linear hydrocarbon aliphatic side chains spaced along said backbone and a plurality of pendant reactive groups which are negatively charged or which may be reacted with compounds having a negative charge depending from said backbone, said linear aliphatic side chains having not over twenty (20) carbon atoms and being substantially embedded in said polymeric substrate.

2. The surface-modified hydrophobic polymeric substrate of claim 1 wherein said linear aliphatic chains each have at least about five carbon atoms.

3. The surface-modified hydrophobic substrate of claim 1 wherein said branched chain polymer has at least about five aliphatic chains.

4. The surface-modified hydrophobic polymeric substrate of claim 1 wherein said branched chain polymer has aliphatic chains substantially regularly spaced from one another.

5. The surface-modified hydrophobic polymeric substrate of claim 1 wherein said branched chain polymer has aliphatic chains which are spaced on the polymer backbone by at least two atoms.

6. The surface-modified hydrophobic polymeric substrate of claim 1 wherein said reactive groups have a negative charge.

7. The surface-modified hydrophobic polymeric substrate of claim 1 wherein said reactive groups are reactive with heparin.

8. The surface-modified hydrophobic polymeric substrate of claim 1 wherein said branched chain polymer has at least about ten aliphatic chains.

9. The surface-modified hydrophobic polymeric substrate of claim 1 wherein said aliphatic pendant chains each have at least about ten carbon atoms.

10. The surface-modified hydrophobic polymeric substrate of claim 1 wherein said linear aliphatic pendant chains are substantially completely embedded in the polymeric substrate.

* * * * *

UNITED STATES PATENT AND TRADEMARK OFFICE
CERTIFICATE OF CORRECTION

PATENT NO. : 4,291,133                                           Page 1 of 4

DATED : September 22, 1981

INVENTOR(S) : Jiri Janata; Vaclav Horak

It is certified that error appears in the above-identified patent and that said Letters Patent is hereby corrected as shown below:

In the drawings, insert FIGS. 1-3 as per attached sheets:

On the title page, "10 Claims, No Drawings" should read
--10 Claims, 3 Drawings--.

UNITED STATES PATENT OFFICE
CERTIFICATE OF CORRECTION

Patent No. 4,291,133      Dated September 22, 1981

Inventor(s) Jiri Janata; Vaclav Horak      Page 2 of 4

It is certified that error appears in the above-identified patent and that said Letters Patent are hereby corrected as shown below:

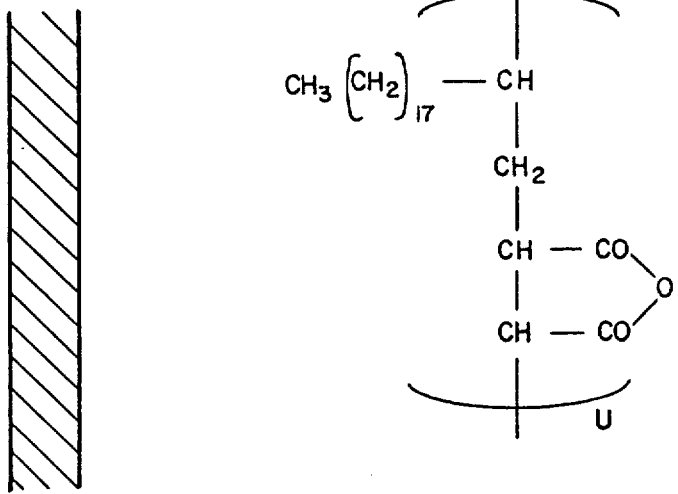

Fig. 1

UNITED STATES PATENT OFFICE
CERTIFICATE OF CORRECTION

Patent No. 4,291,133           Dated September 22, 1981

Inventor(s)  Jiri Janata; Vaclav Horak     Page 3 of 4

It is certified that error appears in the above-identified patent and that said Letters Patent are hereby corrected as shown below:

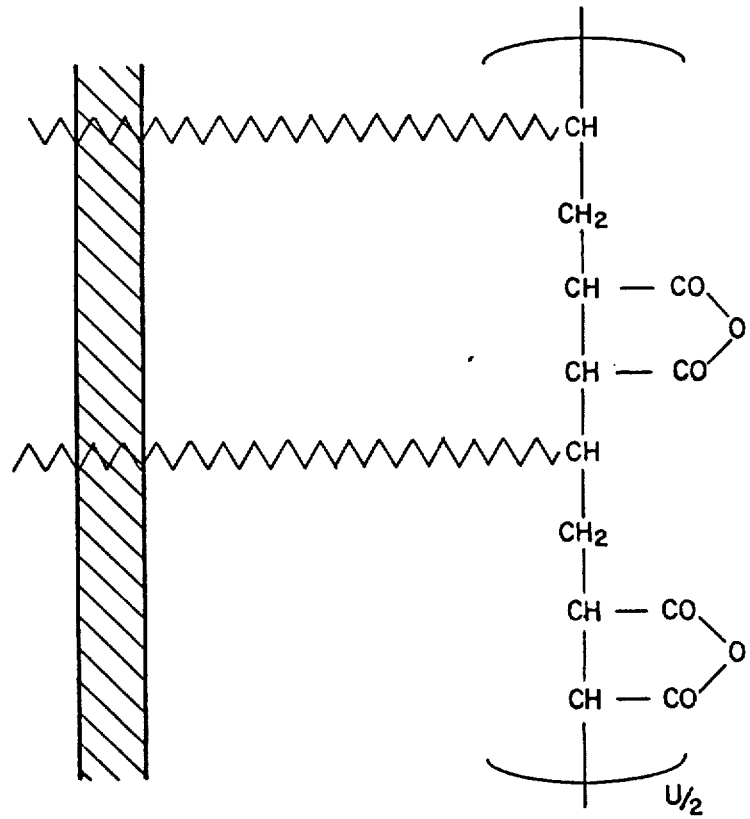

Fig. 2

UNITED STATES PATENT OFFICE
CERTIFICATE OF CORRECTION

Patent No. 4,291,133            Dated September 22, 1981

Inventor(s) Jiri Janata; Vaclav Horak     Page 4 of 4

It is certified that error appears in the above-identified patent and that said Letters Patent are hereby corrected as shown below:

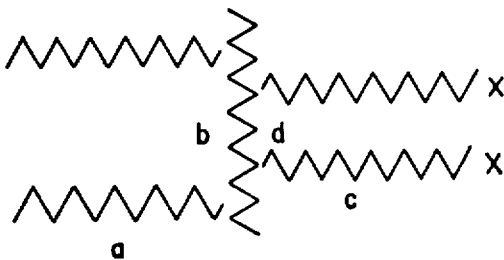

Fig. 3

Signed and Sealed this

Twelfth Day of July, 1988

*Attest:*

DONALD J. QUIGG

*Attesting Officer*     *Commissioner of Patents and Trademarks*